United States Patent
Ferreira et al.

(10) Patent No.: US 8,728,776 B2
(45) Date of Patent: May 20, 2014

(54) BACTERIAL STRAINS AND VARIANTS THEREOF THAT CAN DEGRADE POLYLACTIC ACID, AND USES OF SAME

(75) Inventors: Thierry Ferreira, Iteuil (FR); Willy Aucher, Paris (FR)

(73) Assignees: Centre National de la Recherche Scientifique—CNRS, Paris (FR); Universite de Poitiers, Poitiers (FR)

( * ) Notice: Subject to any disclaimer, the term of this patent is extended or adjusted under 35 U.S.C. 154(b) by 0 days.

(21) Appl. No.: 13/499,339

(22) PCT Filed: Oct. 1, 2010

(86) PCT No.: PCT/FR2010/052076
§ 371 (c)(1),
(2), (4) Date: Mar. 30, 2012

(87) PCT Pub. No.: WO2011/039489
PCT Pub. Date: Apr. 7, 2011

(65) Prior Publication Data
US 2012/0184005 A1 Jul. 19, 2012

(30) Foreign Application Priority Data
Oct. 2, 2009 (FR) ...................................... 09 56898

(51) Int. Cl.
*C12P 7/40* (2006.01)
*C12N 1/12* (2006.01)

(52) U.S. Cl.
USPC ........................................ 435/136; 435/252.1

(58) Field of Classification Search
None
See application file for complete search history.

(56) References Cited

U.S. PATENT DOCUMENTS 6,066,492 A * 5/2000 Tokiwa et al. ............. 435/253.5

FOREIGN PATENT DOCUMENTS

JP 2007 000109 A 11/2007

OTHER PUBLICATIONS

Chang BV et al. Biodegradation of Nonylpenol in Soil. 2007. Chemosphere. 66:1857-1862.*
Akutsu-Shigeno, Yukie et al., "Cloning and sequencing of a poly(DL-lactic acid) depolymerase gene from *Paenibacillus amylolyticus* strain TB-13 and its functional expression in *Escherichia coli*.", Applied and Environmental Microbiology (2003), vol. 69(5), pp. 2498-2504.
Sakai Kenji et al, "Isolation of a thermophilic poly-L-lactide degrading bacterium from compost and its enzymatic characterization", Journal of Bioscience and Bioengineering (2001), vol. 92(3), pp. 1389-1723.
Matsuda Emiko et al., "Gene cloning and molecular characterization of an extracellular poly(L-lactic acid) depolymerase from *Amycolatopsis* sp strain K104-1.", Journal of Bacteriology (2005), vol. 187(21), pp. 7333-7340.
Premraj R. et al., "Biodegradation of polymers" Indian Journal of Biotechnology (2005), vol. 4(2), pp. 186-193.
Shimao M., "Biodegradation of plastics" Current Opinion in Biotechnology (2001), pp. 242-247.
Zuo Yet al., "Isolation of the exoelectrogenic bacterium *Ochrobactrum anthropi* YZ-1 by using a U-tube microbial fuel cell" Applied and Environmental Microbiology (2008), vol. 74(10) pp. 3130-3137.
International Search Report of PCT Application No. FR2010/052076.
Search Report of French Application No. 0956898.
Thoma, Bryan et al., "Identification and antimicrobial susceptibilities of *Ochrobactrum* spp." International Journal of Medical Microbiology (2009), vol. 299, pp. 209-220.

* cited by examiner

*Primary Examiner* — David J Steadman
*Assistant Examiner* — Paul Holland
(74) *Attorney, Agent, or Firm* — McDonnell Boehnen Hulbert & Berghoff LLP

(57) ABSTRACT

The invention relates to strains of bacteria of the genus *Ochrobactrum*, that can degrade polylactic acid. The invention also relates to an enzyme that can degrade polylactic acid, characterized in that it is produced by said bacteria strains according to the invention. The invention also relates to the applications of said bacteria strains and said enzyme that can degrade polylactic acid.

6 Claims, No Drawings

BACTERIAL STRAINS AND VARIANTS THEREOF THAT CAN DEGRADE POLYLACTIC ACID, AND USES OF SAME

FIELD OF THE INVENTION

The invention relates to bacterial strains and the variants of these bacterial strains capable of degrading polylactic acid, and to uses thereof.

INTRODUCTION

Polymer materials, also commonly referred to as "plastics", are encountered in many fields of application owing to their polyvalent physicochemical properties and their low production cost. However, their intensive use over recent decades, coupled with their resistance to degradation, today poses a major problem in the treatment of waste which is associated therewith: by 2010, predictions estimate that the worldwide consumption of plastics will be between 180 and 258 million metric tons.

Despite considerable efforts in waste management, such as the development of recycling circuits, the treatment of plastics still poses many problems and incineration or landfill often remain the only alternatives to their definitive elimination.

Over the last few years, a new generation of materials has appeared on the market: "biodegradable" plastics (ecopolymers or else bioplastics). These are a range of quite particular materials, the formulation of which is suitable for their treatment and their degradation by environmental microorganisms. Unfortunately, the ecopolymers currently available on the market are degradable only under extremely favorable conditions which are not generally encountered in the natural environment.

Among ecopolymers, polylactic acid (PLA) is one of the most promising: it is of natural origin and has been commercially competitive for the past few years owing to the setting up of large-scale production. Furthermore, its physicochemical qualities can allow it to be used in various applications. PLA is considered to be both biodegradable and biocompatible, which makes it possible in particular to use it for producing materials in contact with living tissues (i.e. for biomedical uses such as implants, sutures, encapsidation of molecules of therapeutic interest, etc.). PLA synthesis is a multistep process which begins with the production of lactic acid and ends with the polymerization of the monomers. Since the basic monomers (lactic acid) are obtained by fermentation from renewable resources (carbohydrates), PLA is considered throughout the world to be a material of the future in the context of "sustainable development". In addition, its consumption in 2006 was about 60,000 metric tons per year, although only 30% of the industrially available lactic acid was used for its production. This polymer therefore has considerable potential for development.

Nevertheless, despite all these qualities, the stability of the ester bonds between the lactic acid monomers making up the PLA results in reduced degradability of this material. Indeed, PLA is totally degradable only under industrial compost conditions at temperatures of 60° C. or above. During this process, the degradation of the PLA polymers is the combination of abiotic degradation (by simple hydrolysis of the ester bonds between the monomers, which is accelerated under hot conditions) and, in a second step, biodegradation by the microorganisms of the compost, which hydrolyze the residual oligomers up to the final mineralization step (the whole constituting a "biotic" degradation). Since the use of such temperatures is costly in terms of energy, conventional alternatives for treating this waste remain incineration or landfill, which are particularly harmful from an environmental point of view.

The use of purified microorganisms or enzymes for improving PLA biodegradation has been envisioned. Studies report the degradation of oligomers (molecular weight about 1000 Da) by *Fusarium moniliforme* and *Penicillium roqueforti* (Torres, A. et al., 1996, Screening of microorganisms for biodegradation of poly(lactic-acid) and lactic acid-containing polymers, vol. 62, 2393-2397), and by actinomycetes such as *Amycolatopsis* sp. (Pranamuda, H. et al., 1997 Polylactide Degradation by an *Amycolatopsis* sp, vol. 63, 1637-1640), *Saccharothrix waywayandensis* (Jarerat, A., and Tokiwa, Y., 2003, Biotechnology Letters 25, 401-404), *Kibdelosporangium aridum* (Jarerat, A. et al., 2003, Biotechnology Letters 25, 2035-2038) or by bacteria such as *Bacillus brevis* (Tomita, K., 1999, Journal of Bioscience and Bioengineering 87, 752-755) or else *Paenibacillus amylolyticus* (Teeraphatpornchai, T. et al., 2003, Biotechnology Letters 25, 23-28). Other studies describe PLA degradation by microorganisms belonging to the *Staphylococcus* genus or to the *Streptomyces* genus (U.S. Pat. Nos. 5,25,556 and 6,066,492). Furthermore, the degradation of low-molecular weight PLA (about 2000 Da) by an enzyme of esterase type, such as the lipase of *Rhizopus delemer* has been demonstrated (Fukuzaki, H., 1989, European Polymer Journal 25, 1019-1026). The cutinase-like enzyme of the *Cryptococcus* sp. S2 yeast is also capable of hydrolyzing PLA (Masaki, K., et al., 2005, Cutinase-Like Enzyme from the Yeast *Cryptococcus* sp. Strain S-2 Hydrolyzes Polylactic Acid and Other Biodegradable Plastics 71, 7548-7550).

Finally, studies have shown that certain commercial lipases, and in particular the lipase PL from *Alcaligenes* sp., allow total degradation of PLA in 20 days, but under particular temperature and pH conditions (55° C., pH 8.5) (Hoshino, A., and Isono, Y. (2002). Degradation of aliphatic polyester films by commercially available lipases with special reference to rapid and complete degradation of poly(L-lactide) film by lipase PL derived from *Alcaligenes* sp. Biodegradation 13, 141-147). In the same way, commercial proteases have been tested for this capacity. Some, in particular the alkaline proteases derived from the *Bacillus* genus, and in particular Savinase 16.0L, have been found to be effective. However, none of these enzymes is capable of degrading industrial PLA films (since experimental films have an amorphous surface, they are more susceptible to degradation than industrial films, the structure of which is more crystalline) (Oda, Y. et al., 2000, Degradation of Polylactide by Commercial Proteases. Journal of Polymers and the Environment 8, 29-32). In the end, the commercial enzyme most commonly used for studying PLA biodegradation is proteinase K from *Tritirachium album* (Oda, Y. et al., 2000, Degradation of Polylactide by Commercial Proteases. Journal of Polymers and the Environment 8, 29-32).

Several limitations are nevertheless associated with these processes, and none of them has yet been the subject of industrial development. First of all, in many cases, significant PLA degradation is observed only with purified enzymes, which implies a very high production cost, generally incompatible for uses for common purposes, with relatively moderate added value, such as horticultural pots, for example. The second point is that the microorganisms used are mostly either laboratory strains, or strains isolated from nonconventional environments. As a consequence, most of the enzymatic activities described are in suboptimal conditions in the natural environment. Finally, most of the microorganisms and enzymes tested are capable of hydrolyzing only low-molecular weight oligomers, which is a considerable limit to their use in industrial processes which use large polymers.

There is therefore a real need for new PLA degradation means.

SUMMARY OF THE INVENTION

To their credit, the inventors have isolated a strain of bacteria belonging to the *Ochrobactrum* genus having surprising polylactic acid degradation properties.

The subject of the invention is therefore a strain of bacteria of the *Ochrobactrum* genus, characterized in that said strain is capable of degrading polylactic acid.

The subject of the invention is also a strain of bacteria of the *Ochrobactrum* genus deposited according to the Treaty of Budapest on Jul. 23, 2009, in the name of the Centre National de la Recherche Scientifique, at the Collection Nationale de Cultures de Microorganismes under number CNCM I-4212, or a variant of said strain, said variant being capable of degrading polylactic acid.

The invention also relates to a microorganism mixture, characterized in that it comprises a strain or a variant of said strain according to the invention.

The subject of the invention is also a product comprising a strain or a variant of said strain according to the invention or a microorganism mixture according to the invention, characterized in that said product is in the form of a freeze-dried powder, of a tablet comprising said freeze-dried powder and, optionally, nutrients, or in the form of an aqueous solution.

The invention also relates to an enzyme capable of degrading polylactic acid, characterized in that it is produced by a strain or a variant of said strain according to the invention.

The invention also relates to the use of a strain or of a variant of said strain according to the invention, or of said enzyme according to the invention, for degrading polylactic acid.

The invention also relates to a polylactic acid degradation process, characterized in that it comprises a step consisting in bringing polylactic acid that has to be degraded into contact with a strain or a variant of said strain according to the invention, or with an enzyme capable of degrading polylactic acid according to the invention.

DEFINITIONS

According to the invention, the term "variant" is intended to mean:
- a natural variant of a strain according to the invention, i.e. a variant obtained spontaneously from a strain according to the invention after incubation in a selection medium. A natural variant is therefore obtained without any genetic manipulation by the operator, and only by natural mutation of the strain and selection of this mutated strain in a suitable medium, or
- a variant of a strain according to the invention comprising at least one mutation in its genome, said mutation being induced by genetic engineering, for example by site-directed mutagenesis or random mutagenesis. For example, the random mutagenesis may be carried out using mutagens such as radiation (UV rays, ionizing radiation, heat) or chemical compounds (nitrous acid, ethyl methanesulfonate, N-methyl-N'-nitro-N-nitrosoguanine, N-ethyl-N-nitrosourea, acridine orange, proflavin, etc.).

The term "mutation" is intended to mean the addition, the deletion or the substitution of at least one nucleotide in the genome of the strain according to the invention.

According to the invention, the term "CE medium" or "compost extract" is intended to mean a culture medium for bacteria and variants thereof according to the invention, prepared according to the following process:

Preparation process for 1 L of CE medium:
100 g of compost are infused in qs for 1 L of ultrapure water (MilliQ system from Millipore), with stirring for 16 h (overnight). The mixture is then centrifuged for 1 h at 4000 g, before being subjected to clarifying filtration, carried out using a cellulose filter (Whatman, Grade 4, pores 20-25 μm).

In order to obtain a solid (or "agar") CE medium, agar can be added in an amount of 1.5% (w/v).

The medium is then autoclaved for 20 min at 120° C. (1 bar).

The term "minimum mineral medium" according to the invention is intended to mean a culture medium for bacteria and variants thereof according to the invention, comprising:
10 mg/L $FeSO_4.7H_2O$,
200 mg/L $MgSO_4.7H_2O$,
1 g/L $(NH_4)_2SO_4$,
20 mg/L $CaCl_2.2H_2O$,
100 mg/L NaCl,
0.5 mg/L $Na_2MoO_4.2H_2O$,
0.5 mg/L $Na_2WO_4$,
0.5 mg/L $MnSO_4$,
100 mg/L of yeast extract,
10.7 mM Tris-HCl,
pH 8
ultrapure water (MilliQ system from Millipore), qs.

The medium is then autoclaved for 20 min at 120° C. (1 bar).

The term "ISP2 medium" according to the invention is intended to mean a culture medium for bacteria and variants thereof according to the invention, comprising
yeast extract 4 g/L,
malt extract 10 g/L,
glucose 4 g/L,
ultrapure water (MilliQ system from Millipore), qs.

The medium is then autoclaved for 20 min at 120° C. (1 bar).

DETAILED DESCRIPTION OF THE INVENTION

The subject of the invention is a strain of bacteria of the *Ochrobactrum* genus, characterized in that said strain is capable of degrading polylactic acid.

The subject of the invention is in particular a strain of bacteria of the *Ochrobactrum* genus deposited according to the Treaty of Budapest on Jul. 23, 2009, in the name of the Centre National de la Recherche Scientifique (3 rue Michel Ange, 75794 Paris Cedex 16), at the Collection Nationale de Cultures de Microorganismes (CNCM, Institut Pasteur, 25 rue du docteur Roux, F-75724 Paris Cedex 15) under number CNCM I-4212, or a variant of said strain, said variant being capable of degrading polylactic acid.

The inventors have in fact succeeded in selecting and characterizing a bacterial strain from a garden compost, capable of degrading polylactic acid (PLA). It has been possible to affiliate this strain to the *Ochrobactrum* genus and it has consequently been called *Ochrobactrum* sp. 37S (deposited under number CNCM I-4212).

The *Ochrobactrum* genus has already been isolated for various diversely polluted environment bioremediation properties: strains are capable of degrading solvents such as methyl tert-butyl ether, aromatic compounds, in particular certain phenolic derivatives such as nonylphenols or 2,4,6-tribromophenol, organochlorinated compounds such as the pesticide endosulfan, etc. Moreover, some isolates have shown abilities to sequester heavy metals and to reduce various forms of chromates and dichromates, to degrade vinyl chloride (monomer which is the basis of the plastic PVC) or else to produce emulsifying exopolysaccharides which make it possible to increase hydrocarbon biodegradation. However, to the knowledge of the inventors, no study describes *Ochrobactrum* strains capable of degrading PLA.

An important advantage of the strains of the *Ochrobactrum* genus according to the invention is that they are capable of degrading high-molecular-weight PLA polymers (typically between 110 000 and 120 000 Da) in simple media, both under solid conditions and under liquid conditions. Moreover, the inventors have been able to demonstrate that the *Ochrobactrum* sp. 37S strain (CNCM I-4212) has the property of degrading PLA when it is cultured on a CE medium (compost extract), which is produced by simple infusion of compost in water.

All these observations therefore show that the strains of the *Ochrobactrum* genus according to the invention, and in particular the *Ochrobactrum* sp. 37S strain (CNCM I-4212) and variants thereof, are excellent candidates for numerous applications aimed at improving PLA degradation, in particular under industrial compost conditions.

The ability of these strains and of the variants thereof according to the invention to degrade polylactic acid can be evaluated by any method known by those skilled in the art. In particular, the ability of the strains and of the variants thereof according to the invention to degrade polylactic acid can be typically evaluated by means of a Test A comprising the following steps:
1) inoculating, via the streaking method, a Petri dish comprising a minimum mineral agar medium supplemented with emulsified polylactic acid at 1 g/L, using a liquid culture in the same medium comprising $10^8$ to $10^9$ CFU/mL, of said strain or of said variant for which it is desired to evaluate the ability to degrade polylactic acid,
2) incubating the Petri dish inoculated in step (1) in a humid incubator (86-88% humidity) for 22 days at 37° C., and
3) detecting the possible presence of a translucent zone around the colonies having grown on the Petri dish, said translucent zone revealing the ability of said strain or said variant tested to degrade polylactic acid.

The "streaking method" is well known to those skilled in the art. It typically consists in inoculating the Petri dish using a platinum loop immersed beforehand in a liquid culture of bacteria, and making streaks in a backward and forward motion at the surface of the agar medium.

In order to obtain the minimum mineral medium supplemented with polylactic acid as used in step 1 of Test A according to the invention, 1 g/L of polylactic acid with a molecular weight of between 110,000 and 120,000 Da is emulsified in a minimum mineral medium according to the invention. The emulsion is prepared in the following way:

PLA in powder form (polymers of molecular weight between 110,000 and 120,000 Da, Valagro, Poitiers, France) is first of all solubilized in dichloromethane (50 g/L of dichloromethane), before being added to the medium of interest at the final concentration of 1 g/L. The mixture is then homogenized by dispersion of the PLA in the medium using an Ultraturax®, at maximum speed, for 30 to 40 s. The medium is then immediately autoclaved (20 min, 120° C., 1 bar), in order to prevent the formation of aggregates.

Finally, in order to obtain an agar medium, 1.5% (w/v) of agar is added to said minimum mineral medium supplemented with polylactic acid. This minimum mineral agar medium supplemented with emulsified polylactic acid at 1 g/L is then poured into Petri dishes.

The invention also relates to a microorganism mixture, characterized in that it comprises a strain or a variant of said strain according to the invention. In particular, this microorganism mixture may comprise other microorganisms having the property of degrading polylactic acid. Typically, these microorganisms are bacteria or fungi. More particularly, these microorganisms can be chosen from bacteria belonging to the phylum Firmicutes (*Firmus cutis*), having the property of degrading low-molecular-weight PLA polymers (less than or equal to 20,000 Da), as described by Mayumi et al. (Mayumi, D. et al. (2008), Applied Microbiology and Biotechnology 79, 743-750). Other examples of bacteria are the bacteria of the class of bacilli, in particular the *Bacillus cereus* spp. bacterial strains or the *Bacillus clausii* spp. bacterial strains.

The strains and variants thereof according to the invention and also the microorganism mixtures according to the invention are typically prepared in varied forms. The invention therefore also relates to a product (or a composition) comprising a strain or a variant of said strain according to the invention or a microorganism mixture according to the invention, characterized in that said product (or said composition) is in the form of a freeze-dried powder, of a tablet comprising said freeze-dried powder and, optionally, nutrients (such as vitamins, mineral salts, etc.), or in the form of an aqueous solution. Typically, said aqueous solution is obtained by culturing at least one strain or a variant thereof according to the invention or optionally a microorganism mixture according to the invention, in a suitable culture medium, such as the minimum mineral medium according to the invention or the CE medium (compost extract) according to the invention.

The invention also relates to an enzyme capable of degrading polylactic acid, characterized in that it is produced by a strain or a variant of said strain according to the invention. Typically, this enzyme, or PLA depolymerase, can be characterized by cloning of the gene encoding said enzyme. This characterization of the enzyme by cloning can in particular be carried out according to a process adapted from that described by Mayumi, D. et al., 2008, Applied Microbiology and Biotechnology 79, 743-750. Typically, the characterization of the enzyme by cloning the gene encoding said enzyme comprises the following steps:
1) the DNA purified from a culture of the *Ochrobactrum* sp. 37S strain (deposited under number CNCM I-4212) cultured in complete ISP2 medium is extracted and then partially digested using the Sau3AI enzyme;
2) the fragments obtained of between 2 and 4 kb are then cloned into the pUC18 plasmid (Toyobo, Osaka, Japan), digested beforehand with the BamHI enzyme;
3) the recombinant plasmids are inserted by transformation into the *E. coli* DH5α recipient strain;
4) 40 000 clones of transformed *E. coli* DH5α bacteria (statistically covering the entire genome of the *Ochrobactrum* sp. 37S strain) are plated out, in a proportion of approximately 500 clones per dish, on Petri dishes comprising an LB (Luria-Bertani) agar medium covered with a medium comprising 1 g/L of emulsified PLA (molecular weight between 110,000 and 120,000 Da) and 1.5% of agar (medium adapted from Akutsu-Shigeno Y. et al., 2003, vol. 69, 2498-2504);
5) the plasmids are extracted from the bacteria forming a translucent zone on the Petri dishes;

6) the gene encoding the enzyme (PLA depolymerase) is finally identified by sequencing of the insert and comparison with the known enzyme sequences (BLAST).

In order to facilitate the subsequent enzyme purification steps, a tag corresponding to a His•Tag® unit is typically introduced, after cloning of the gene of interest in a bacterial expression plasmid of pET-24a(+) type (Novagen, Madison, USA). The enzyme can then be purified in one step, by passing a crude enzymatic extract (obtained after sonication of the transformed bacterial strain) over a nickel column (Pharmacia, Biotech, Upsala, Sweden). The PLA depolymerase activity in the fractions eluted from the column is then determined by measuring the decrease in turbidity of a PLA emulsion, as described by Teeraphatpornchai et al. (2003, Biotechnology Letters, 25, 23-28). The fractions exhibiting the PLA depolymerase activity are then pooled, and then concentrated by ultracentrifugation (YM10 membranes; Millipore, Bedford, USA).

The invention also relates to the use of a strain or a variant of said strain according to the invention, of or an enzyme according to the invention, for degrading polylactic acid.

The invention also relates to a process for degrading polylactic acid, characterized in that it comprises a step consisting in bringing polylactic acid that has to be degraded into contact with a strain or a variant of said strain according to the invention, or with an enzyme capable of degrading polylactic acid according to the invention.

In one particular embodiment, said step consisting in bringing the polylactic acid that has to be degraded into contact with a strain or a variant of said strain according to the invention consists in inoculating said polylactic acid that has to be degraded with a strain or a variant of said strain according to the invention.

The process according to the invention is therefore particularly suitable for degrading polylactic acid in media comprising polylactic acid or in media comprising a material made up of the whole or a part of polylactic acid, such as typically a mixture of domestic or industrial waste, a mixture of organic waste, in particular a compost, liquid manure, activated sludge, etc.

The process for degrading polylactic acid according to the invention therefore has many applications, in particular for treating waste comprising polylactic acid. Moreover, the process for degrading polylactic acid according to the invention has the advantage of not producing greenhouse gases, unlike conventional incineration processes. Moreover, a major advantage of the process according to the invention is the conversion, by the bacteria and variants thereof according to the invention or by the enzyme according to the invention, of the PLA into a recoverable organic substance, in particular into organic acids.

Typically, the polylactic acid or PLA degraded by the strains of bacteria or variants thereof according to the invention is chosen from:
- a homopolymer of lactic acid of L conformation,
- a homopolymer of lactic acid of D conformation,
- a copolymer of lactic acid of L conformation and of lactic acid of D conformation, or
- a copolymer of at least any one of the polymers mentioned above with another polymer, the lactic acid representing at least 90% by weight of the composition of said copolymer.

Still typically, the polylactic acid or PLA degraded by the strains of bacteria or variants thereof according to the invention also comprises a material made up of the whole or a part of polylactic acid as defined above. According to the invention, a material consisting partly of polylactic acid is typically a material partly made up of polylactic acid as defined above and partly made up of at least one other constituent, such as in particular at least one other bioplastic (ecopolymer) or a nonbiodegradable plastic.

In one particular embodiment, said polylactic acid degraded by the strains of bacteria or variants thereof according to the invention is a polylactic acid of which the molecular weight is less than 140,000 Da, in particular between 2000 and 140,000 Da. Quite particularly, said polylactic acid degraded by the strains of bacteria or variants thereof according to the invention has a molecular weight of between 100,000 and 130,000 Da, even more particularly between 110,000 and 120,000 Da.

Other aspects and advantages of the present invention are described in the following examples, which should be considered by way of illustration and as not limiting the scope of the invention.

EXAMPLES

1. Isolation of the CNCM I-4212 Strain:
A strain having the ability to degrade PLA was isolated from a garden compost as follows:
- a sheet of PLA (85 mm×120 mm×1 mm; molecular weight from 110 000 to 120 000 Da, Valagro, Poitiers, France) was incubated in a simple garden compost (Iteuil, Vienne département [the Vienne county], France), for 45 days. The biological material having developed at the surface of the PLA sheet (biofilm) was then recovered by scraping using a metal spatula;
- 100 mg of biofilm were then resuspended in 1 mL of phosphate buffer (0.1 M, pH 7). 250 µL of this suspension were then used to inoculate a liquid CE medium containing an emulsion of PLA (polymers of molecular weight between 110,000 and 120,000 Da) at 1 g/L, prepared as described in paragraph 3.2.2 hereinafter ("CE liquid medium+PLA"). The resulting preculture was incubated for 3 days at 37° C., with shaking (200 rpm);
- a step of enrichment (multiplication) of the bacterial strain in said CE liquid medium+PLA was then carried out by means of two successive re-inoculations ($10^{-1}$ dilutions) in 5 mL of the same medium, and under the same conditions (3 days of incubation at 37° C. and with shaking);
- finally, an aliquot of the final culture was removed in order to obtain a suspension in sterile milliQ water, at a dilution of $10^{-5}$. 100 µL of this dilution were then plated out on a CE agar medium containing an emulsion of PLA (polymers of molecular weight between 110,000 and 120,000 Da) at 1 g/L, prepared as described in paragraph 3.1.2 hereinafter. The dishes were then incubated in an incubator for 22 days at 37° C.

On this medium, a colony surrounded by a translucent zone, reflecting the degradation of the PLA, was isolated. This strain was recovered, re-suspended and plated out on the same medium using the streaking method.

2. Identification of the CNCM I-4212 Strain:
The growth of the strain isolated (cf. §1.) was first of all tested in various liquid complete media. It was possible to show that this strain grows strongly in an ISP2 medium (yeast extract 4 g/L, malt extract 10 g/L, glucose 4 g/L, purified water qs). The total DNA was extracted from a liquid culture in this medium, as described by Schäfer and Muyzer (Schäfer, H., and Muyzer, G. (2001) Methods in Microbiology, vol. 30, ed. J. H. Paul, London: Academic Press, 425-468). A portion of the gene encoding the 16S RNA was then amplified using specific primers (SEQ ID NO 1 and SEQ ID NO 2) and sequenced.

The sequences of the primers used for the characterization are the following (Muyzer G. et al. (1993), Appl. Environ. Microbiol. 59, 695-700):

341F-GC:
(SEQ ID NO 1)
5'CGCCCGCCGCGCCCCGCGCCCGTCCCGCCGCCCCGCCCGCCTACGGG
AGGCAGCAG3' and

907R:
(SEQ ID NO 2)
5'CCGTCAATTCCTTTRAGTTT3'

Comparison of the sequence obtained, with the databases (Blast, ch.embnet.org), made it possible to affiliate the strain to the *Ochrobactrum* genus after production of a phylogenetic tree. The CNCM I-4212 strain was therefore denoted by the inventors under the following name: *Ochrobactrum* sp. 37S.

3. Polylactic Acid Degradation:

3.1. In Agar Medium:

The ability of the CNCM I-4212 strain to degrade polylactic acid with a molecular weight of between 110,000 and 120,000 Da was tested on various agar media supplemented with PLA.

3.1.1. Minimum Mineral Agar Medium Supplemented with Polylactic Acid with a Molecular Weight of Between 110,000 and 120,000 Da:

In order to obtain said minimum mineral medium supplemented with polylactic acid, 1 g/L of polylactic acid with a molecular weight of between 110,000 and 120,000 Da was emulsified in a minimum mineral medium according to the invention. The emulsion is prepared in the following way:

PLA in powder form (polymers of molecular weight between 110,000 and 120 000 Da, Valagro, Poitiers, France), is first of all solubilized in dichloromethane (50 g/L of dichloromethane), before being added to the medium of interest at the final concentration of 1 g/L. The mixture is then homogenized by dispersion of the PLA in the medium using an Ultraturax®, at maximum speed, for 30 to 40 s. The medium is then immediately autoclaved (20 min, 120° C., 1 bar), in order to prevent aggregate formation. Finally, in order to obtain an agar medium, 1.5% (w/v) of agar is added to said minimum mineral medium supplemented with polylactic acid. This minimum mineral agar medium supplemented with emulsified polylactic acid at 1 g/L is then poured into Petri dishes.

3.1.2. CE Agar Medium Supplemented with Polylactic Acid with a Molecular Weight of Between 110,000 and 120, 000 Da:

In order to obtain said CE medium supplemented with polylactic acid, 1 g/L of polylactic acid with a molecular weight of between 110,000 and 120,000 Da was emulsified in a CE medium according to the invention, as described in paragraph 3.1.1. In order to obtain an agar medium, 1.5% (w/v) of agar is added to said CE medium supplemented with polylactic acid, and then it is poured into Petri dishes.

3.1.3. Inoculation

Petri dishes prepared as described in paragraphs 3.1.1. and 3.1.2. were inoculated, by the streaking method, using a liquid culture (CE medium or minimum mineral medium) comprising $10^8$ to $10^9$ CFU/mL of the CNCM I-4212 strain. The dishes were then incubated in an incubator for 22 days at 37° C.

3.1.4. Observations

The PLA degradation was evaluated over time (from 5 to 22 days after inoculation) through the appearance of a clear translucent zone around the colonies of the strain of bacteria according to the invention.

After 22 days of incubation, regardless of the culture medium used, the colonies of the strain of bacteria according to the invention were surrounded by a clear translucent zone reflecting the PLA degradation.

However, culturing on a minimum mineral agar medium supplemented with polylactic acid makes it possible to accelerate the PLA degradation compared with that observed on a CE agar medium supplemented with polylactic acid.

3.2. In Liquid Medium:

The ability of the CNCM I-4212 strain to degrade polylactic acid with a molecular weight of between 110,000 and 120,000 Da was also evaluated in liquid medium.

3.2.1. Minimum Mineral Liquid Medium Supplemented with Polylactic Acid with a Molecular Weight of Between 110,000 and 120,000 Da:

In order to obtain the minimum mineral liquid medium supplemented with polylactic acid, 1 g/L of polylactic acid with a molecular weight of between 110,000 and 120,000 Da was emulsified in a minimum mineral medium according to the invention. The emulsion was prepared as described in paragraph 3.1.1.

3.2.2. CE Liquid Medium Supplemented with Polylactic Acid with a Molecular Weight of Between 110,000 and 120, 000 Da:

In order to obtain the CE liquid medium supplemented with polylactic acid, 1 g/L of polylactic acid with a molecular weight of between 110,000 and 120,000 Da was emulsified in a CE medium according to the invention, as described in paragraph 3.1.1.

3.2.3. Inoculation 200 mL of CE medium or of minimum mineral medium, prepared as described in paragraphs 3.2.1 and 3.2.2, were inoculated, or not (controls), with approximately $5 \times 10^9$ CFU of the CNCM I-4212 strain, and then incubated for 30 days at 37° C. with shaking at 150 rpm.

3.2.4. Observations

Once the incubation had ended (D+30), the PLA was extracted from the culture media with dichloromethane. More specifically, 200 mL of dichloromethane were added to the 200 mL of culture. After obtaining a homogeneous phase by vigorous stirring, the mixture is decanted for 10 min, before removing the upper phase and transferring said phase to a 1 L glass beaker. After complete evaporation of the solvent (3 days in a fume cupboard (Sorbonne)), the remaining PLA (not degraded) is observed through the appearance of a brown deposit in the beaker. The results show that the deposit of remaining PLA is significantly decreased in the presence of the CNCM I-4212 strain. The same results were obtained regardless of the culture medium.

These results demonstrate that the CNCM I-4212 strain is capable of degrading high-molecular-weight PLA polymers under liquid conditions, and what is more in a simple medium composed of a compost extract, the CE medium.

Throughout the description of the invention, literature references from the prior art are mentioned. The content of these references is incorporated into the present description here by way of reference.

The invention claimed is:

1. An isolated *Ochrobactrum* sp. 37S deposited according to the Treaty of Budapest on Jul. 23, 2009, in the name of the Centre National de la Recherche Scientifique, at the Collection Nationale de Cultures de Microorganismes under accession number CNCM I-4212, said bacterium being capable of degrading polylactic acid.

2. A microorganism mixture, comprising the isolated *Ochrobactrum* sp. 37S of claim 1.

3. A product comprising the isolated *Ochrobactrum* sp. 37S of claim 1, wherein said product is in the form of a freeze-dried powder, a tablet comprising said freeze-dried powder and, optionally, nutrients, or in the form of an aqueous solution.

4. A process for degrading polylactic acid, comprising contacting polylactic acid with the isolated *Ochrobactrum* sp. 37S of claim 1.

5. The process as claimed in claim 4, wherein said polylactic acid has a molecular weight of less than 140,000 Da.

6. A product comprising the microorganism mixture of claim 2, wherein said product is in the form of a freeze-dried powder, a tablet comprising said freeze-dried powder and, optionally, nutrients, or in the form of an aqueous solution.

* * * * *

SEQUENCE LISTING

```
<160> NUMBER OF SEQ ID NOS: 2

<210> SEQ ID NO 1
<211> LENGTH: 57
<212> TYPE: DNA
<213> ORGANISM: Artificial
<220> FEATURE:
<223> OTHER INFORMATION: primer sequence

<400> SEQUENCE: 1
cgcccgccgc gccccgcgcc cgtcccgccg ccccgcccg cctacgggag gcagcag        57

<210> SEQ ID NO 2
<211> LENGTH: 20
<212> TYPE: DNA
<213> ORGANISM: Artificial
<220> FEATURE:
<223> OTHER INFORMATION: primer sequence

<400> SEQUENCE: 2
ccgtcaattc ctttragttt                                                20
```